United States Patent [19]

Kossovsky et al.

[11] Patent Number: 5,460,831
[45] Date of Patent: * Oct. 24, 1995

[54] TARGETED TRANSFECTION NANOPARTICLES

[75] Inventors: Nir Kossovsky; H. James Hnatyszyn; Andrew Gelman, all of Los Angeles, Calif.

[73] Assignee: The Regents of the University of California, Oakland, Calif.

[*] Notice: The portion of the term of this patent subsequent to Jan. 12, 2010 has been disclaimed.

[21] Appl. No.: 147,751

[22] Filed: Nov. 4, 1993

Related U.S. Application Data

[63] Continuation-in-part of Ser. No. 199, Jan. 4, 1993, Pat. No. 5,334,394, which is a continuation-in-part of Ser. No. 690,601, Apr. 24, 1991, Pat. No. 5,178,882, which is a continuation-in-part of Ser. No. 542,255, Jun. 22, 1990, Pat. No. 5,219,577.

[51] Int. Cl.$^6$ .................................................. A61K 9/14
[52] U.S. Cl. .......................... 424/493; 424/490; 424/494; 424/498; 424/204.1; 514/951; 514/970
[58] Field of Search .................... 424/493, 494, 424/490, 498

[56] References Cited

U.S. PATENT DOCUMENTS

| | | | |
|---|---|---|---|
| 4,501,726 | 2/1985 | Schröder et al. | 424/1.1 |
| 4,904,479 | 2/1990 | Illum | 424/490 |
| 5,178,882 | 1/1993 | Kossovsky et al. | 424/494 |
| 5,219,577 | 6/1993 | Kossovsky et al. | 424/494 |

*Primary Examiner*—Thurman K. Page
*Assistant Examiner*—James M. Spear
*Attorney, Agent, or Firm*—Poms, Smith, Lande & Rose

[57] ABSTRACT

A biologically active composition for use in gene therapy and other transfection procedures. The composition is composed of nanocrystalline core particles which are coated with a layer that is designed to allow attachment of transfection agents (DNA/RNA segments or antisense fragments) without denaturing them. The composition may further include an exterior targeting membrane which provides selective targeting of the transfection agents to specific cell receptors.

16 Claims, No Drawings

TARGETED TRANSFECTION NANOPARTICLES

This is a continuation-in-part of application Ser. No. 08/000,199, now U.S. Pat. No. 5,334,394 which was filed on Jan. 4, 1993 which is a continuation-in-part of Ser. No. 07/690,601 which was filed on Apr. 24, 1991, now U.S. Pat. No. 5,178,882 which is a continuation-in-part of application Ser. No. 07/542,255 which was filed on Jun. 22, 1990, now U.S. Pat. No. 5,219,577.

BACKGROUND OF THE INVENTION

1. Field of the Invention

The present invention relates generally to synthetic biologically active compositions which have a microparticulate (nanoparticulate) core. More particularly, the present invention relates to biologically active compositions where transfecting DNA or RNA is attached to a microparticulate core and coated with a targeting membrane or ligand. These transfection nanoparticles are useful in delivering the transfecting DNA or RNA to target cells.

2. Description of Related Art

The attachment of biologically active proteins, peptides or pharmacologic agents to various carrier particles has been an area of intense investigation. These conjugated biological systems offer the promise of reduced toxicity, increased efficacy and lowered cost of biologically active agents. As a result, many different carrier models are presently available. (Varga, J. M., Asato, N., in Goldberg, E. P. (ed.): *Polymers in Biology and Medicine*. New York, Wiley, 2, 73–88 (1983). Ranney, D. F., Huffaker, H. H., in Juliano, R. L. (ed.): *Biological Approaches to the Delivery of Drugs, Ann. New York Acad. Sci.*, 507, 104–119 (1987).) Nanocrystalline and micron sized inorganic substrates are the most common carriers and proteins are the most commonly conjugated agents. For example, gold/protein (principally immunoglobulin) conjugates measuring as small as 5 nm have been used in immunological labeling applications in light, transmission electron and scanning electron microscopy as well as immunoblotting. (Faulk, W., Taylor, G., *Immunochemistry* 8, 1081–1083 (1971). Hainfeld, J. F., *Nature* 333, 281–282 (1988).)

Silanized iron oxide protein conjugates (again principally antibodies) generally measuring between 500 and 1500 nm have proven useful in various in vitro applications where paramagnetic properties can be used advantageously. (Research Products Catalog, Advanced Magnetics, Inc., Cambridge, Mass., 1988–1989.) Ugelstad and others have produced gamma iron oxides cores coated with a thin polystyrene shell. (Nustad, K., Johansen, L., Schmid, R., Ugelstad, J., Ellengsen, T., Berge, A.: Covalent coupling of proteins to monodisperse particles. Preparation of solid phase second antibody. Agents Actions 1982; 9:207–212 (id. no. 60).) The resulting 4500 nm beads demonstrated both the adsorption capabilities of polystyrene latex beads as well as the relatively novel benefit of paramagnetism.

Carrier systems designed for in vivo applications have been fabricated from both inorganic and organic cores. For example, Davis and Illum developed a 60 nm system comprised of polystyrene cores with the block copolymer poloxamer, polyoxyethylene and polyoxypropylene, outer coats that showed a remarkable ability to bypass rat liver and splenic macrophages. (Davis, S. S., Illum, L., *Biomaterials* 9, 111–115 (1988)). Drug delivery with these particles has not yet been demonstrated. Ranney and Huffaker described an iron-oxide/albumin/drug system that yielded 350–1600 nm paramagnetic drug carriers. (Ranney, D. F., Huffaker, H. H., In, Juliano, R. L. (ed.): *Biological approaches to the delivery of drugs, Ann. New York Acad. Sci.* 507, 104–119 (1987).) Poznasky has developed an enzyme-albumin conjugate system that appears to decrease the sensitivity of the product to biodegradation while masking the apparent antigenicity of the native enzyme. (Poznasky, M. J.: Targeting enzyme albumin conjugates. Examining the magic bullet. In, Juliano, R. L. (ed.): *Biological approaches to the delivery of drugs*, Annals New York Academy Sciences 1987; 507-211:219.)

Shaw and others have prepared and characterized lipoprotein/drug complexes. (Shaw, J. M., Shaw, K. V., Yanovich, S., Iwanik, M., Futch, W. S., Rosowsky, A., Schook, L. B.: Delivery of lipophilic drugs using lipoproteins. In, Juliano, R. L.(ed.): *Biological approaches to the delivery of drugs*, Annals New York Academy Sciences 1987; 507:252–271.) Lipophilic drugs are relatively stable in these carriers and cell interactions do occur although little detail is known.

In any conjugated biological composition, it is important that the conformational integrity and biological activity of the adsorbed proteins or other biological agents be preserved without evoking an untoward immunological response. Spacial orientation and structural configuration are known to play a role in determining the biological activity of many peptides, proteins and pharmacological agents. Changes in the structural configuration of these compounds may result in partial or total loss of biological activity. Changes in configuration may be caused by changing the environment surrounding the biologically active compound or agent. For example, pharmacologic agents which exhibit in vitro activity may not exhibit in vivo activity owing to the loss of the molecular configuration formerly determined in part by the in vitro environment. Further, the size and associated ability of the carrier particle to minimize phagocytic trapping is a primary concern when the composition is to be used in vivo. All of these factors must be taken into account when preparing a carrier particle.

To date, gene therapy in humans has been limited to ex-vivo protocols in which tissues are transfected in the culture dish and placed back in the body. In vivo work is still in pre-clinical development and has been confined to animal models due to a range of safety and efficacy issues. Such concerns arise primarily from the use of viral vectors to effect the gene transfer. Retroviral transfection has generated a lot of interest since it can stably transfect nearly 100% of targeted cells ex-vivo. Production of transfecting, replication defective retroviruses, proceeds through packaging cell lines which in principle are unable to produce wild type virus. However, low titers of "wild type" (replication competent) virus have been observed in these systems. In one such protocol utilizing primates, outbreaks of lymphoma were linked to the detection of wild type retrovirus from a packaging system. Besides potential pathogenicity, maintaining useful transfecting titers of these vectors can be difficult. They are hard to purify and concentrate since the envelopes (membranes) tend to be extremely labile. Alternatively, adenoviral vectors have been found to be considerably more stable. Moreover, these viruses are capable of transfecting quiescent tissue and producing large amounts of gene products. Unfortunately, gene expression is often transient because the viral genome often remains extrachromosomal. Direct clinical application is also problematic, since replication of the vector can result in aberrant host protein synthesis leading to deleterious effects ranging from oncogenesis to cellular toxicity.

Given the practical concerns of in vivo viral transfection, nonviral methods are also being developed. At present, most efforts are centered on receptor mediated transfer because such methods can provide targeted delivery of DNA (and RNA) in vivo. Receptor-mediated systems employ ligand DNA (and RNA) complexes which can be recognized by cell receptors on the cell surface. Internalization of the complex occurs via the formation of endocytotic vesicles which allow for transport into the cytoplasm. Problems arise, however, when the endosomes fuse with lysosomes which causes the contents to be destroyed. In turn, the transfection rate for these complexes remain below clinical efficacy. Some investigators have used fusogenic peptides of Influenza Hemmoglutin A to disrupt endosome formation which has led to higher transfection rates. Nonetheless, the data on in vivo expression suggests that this method may only permit transient expression of genes.

Besides ligand DNA (and RNA) complexes, lipofection techniques have also been tried with varying success. Liposomes are specially susceptible to uptake by the filter organs and in the peripheral tissues by macrophages which limits their transfection efficiency and specificity in vivo.

In view of the above, it would be desirable to provide compositions which can be used to transfect cells with DNA or RNA in both in vivo or in vitro environments.

SUMMARY OF THE INVENTION

In accordance with the present invention, transfecting DNA or RNA is attached to a nanocrystalline core particle and coated with a targeting ligand or membrane to provide a viral transfection system which may be used in gene therapy. The invention is based in part on the discovery that the surface of ultrafine particles (nanocrystalline particles) can be modified with a surface coating to allow attachment of transfecting DNA or RNA to produce compositions wherein the naturally occurring structural environment of the DNA or RNA is mimicked sufficiently so that biological activity is preserved. The core particle, with the surface coating and attached transfecting DNA or RNA, is further coated with a targeting agent, such as ligand or phospholipid membrane complex to provide targeting of the DNA or RNA to particular cell receptors.

As a feature of the present invention, the nanocrystalline core may be composed of brushite. This material is biodegradable, inexpensive and is found in human beings as a substrate of bone synthesis. The brushite particles may be synthesized at a nanomeric size (between approximately 5 nm and 150 nm). This small size allows the DNA/RNA delivery construct to be small enough to avoid uptake by the Reticulo-Endothelial System (RES) of the body and deliver the DNA/RNA to cells in vivo without non-specific toxicity or loss of drug to macrophages.

As a feature of the present invention, the DNA/RNA particle construct is targeted to a specific tissue or cell type. In order to achieve this targeting, the construct has a targeting ligand or a primed phospholipid membrane tightly adsorbed to its surface. The membrane may contain proteins, receptors and carbohydrates which provide targeting of the vehicle. The membrane also serves to further maintain the stability of the transfecting DNA or RNA and the integrity of the construct. This membrane may be derived from cell membranes, viral envelopes (see U.S. Pat. No. 5,178,882), or other specifically engineered or synthesized membranes. Due to the very small size of the biodegradable core particle delivery system, multiple layers of membranes may be adsorbed to the core particle to increase the efficiency of targeting. The DNA/RNA transfecting microparticles in accordance with the present invention have wide-ranging use depending upon the particular DNA or RNA which is attached to the biodegradable microparticle core.

The above-discussed and many other features and attendant advantages of the present invention will become better understood by reference to the following detailed description.

DETAILED DESCRIPTION OF THE INVENTION

The present invention has wide application to procedures and methods wherein DNA or RNA are delivered, i.e. transfected, to cells in vivo or in vitro. These areas of application include gene therapy. The compositions of the present invention can be used in a wide variety of other applications where there is a need to target DNA or RNA to particular cell types in both in vivo and in vitro environments. The invention may also be used to target other transfection agents, such as antisense fragments. The term "transfection agent" as used herein is intended to mean DNA or RNA segments or antisense fragments which are capable of transfection into a cell. Exemplary transfection agents include sense DNA, sense RNA, antisense RNA, and antisense DNA.

The compositions of the present invention include nanocrystalline core particles (diameters of less than 1000 nm) which are coated with a surface energy modifying layer that promotes bonding of proteins, peptides or pharmaceutical agents to the particles. The coating modifies the surface energy of the nanocrystalline core particles so that DNA and RNA segments may be attached to the core particle without significant loss of activity or denaturization. The result is a biochemically active composition which includes a biochemically inert core. The end use for the compositions of the present invention will depend upon the particular transfection agent which is attached to the coated core particle. For example, DNA segments, such as human low density lipid receptor, are used in gene therapy. RNA segments, such as antisense and sense MRNA, are used in the transfection procedure. Antisense fragments, such as HIV reverse transcriptase are used in the transfection particles. Preferred particle sizes are on the order of 10 nm to 150 nm.

The core particles may be made from a variety of inorganic materials including metals or ceramics. Preferred metals and alloys include beryllium, silicon, gallium, copper, gold, titanium, nickel, aluminum, silver, iron, steels, cobalt-chrome alloys, and titanium alloys. Preferred ceramic materials include brushite, tricalcium phosphate, alumina, silica, and zirconia. The core particles may be made from organic materials including carbon (diamond). Preferred polymers include polystyrene, silicone rubber, polycarbonate, polyurethanes, polypropylenes, polymethylmethaacrylate, polyvinyl chloride, polyesters, polyethers, and polyethylene. Particles made from brushite, are particularly preferred.

Particles made from the above materials having diameters less than 1000 nanometers are available commercially or they may be produced from progressive nucleation in solution (colloid reaction), or various physical and chemical vapor deposition processes, such as sputter deposition (Hayashi, C., *J. Vac. Sci. Technol.* A5 (4), July/August 1987, pgs. 1375–1384; Hayashi, C., *Physics Today*, December 1987, pgs. 44–60; MRS Bulletin, January 1990, pgs. 16–47).

Plasma-assisted chemical vapor deposition (PACVD) is one of a number of techniques that may be used to prepare suitable microparticles. PACVD functions in relatively high atmospheric pressures (on the order of one torr and greater) and is useful in generating particles having diameters of up to 1000 nanometers. For example, aluminum nitride particles having diameters of less than 1000 nanometer can be synthesized by PACVD using Al $(CH_3)_3$ and $NH_3$ as reactants. The PACVD system typically includes a horizontally mounted quartz tube with associated pumping and gas feed systems. A susceptor is located at the center of the quartz tube and heated using a 60 KHz radio frequency source. The synthesized aluminum nitride particles are collected on the walls of the quartz tube. Nitrogen gas is used as the carrier of the Al $(CH_3)^3$. The ratio of Al $(CH_3)^3$: $NH_3$ in the reaction chamber is controlled by varying the flow rates of the $N_2$/Al$(CH_3)_3$ and $NH_3$ gas into the chamber. A constant pressure in the reaction chamber of 10 torr is generally maintained to provide deposition and formation of the ultrafine nanocrystalline aluminum nitride particles. PACVD may be used to prepare a variety of other suitable biodegradable nanocrystalline particles.

The core particles are coated with a substance that provides a threshold surface energy to the particle or other surface which is sufficient to cause binding to occur without that binding being so tight as to denature biologically relevant sites. Coating is preferably accomplished by suspending the particles in a solution containing the dispersed surface modifying agent. It is necessary that the coating make the surface of the particle more amenable to protein or peptide attachment.

Suitable coating substances in accordance with the present invention include carbohydrates, carbohydrate derivatives, and other macromolecules with carbohydrate-like components characterized by the abundance of —OH (hydroxyl) side groups. The coatings may include but are not limited to:

- short chain carbohydrates including glucose, sucrose, cellobiose, nystose, triose, dextrose, trehalose, glucose, lactose, maltose, etc.
- hydroxyl rich weak acids such as citrate, fumarate, succinate, isocitrate, oxaloacetate, malate, etc.
- nucleotide-like molecules with pendant carbohydrate or phosphate groups such as pyridoxyl-5-pyrophosphate, thiamine pyrophosphate, uridinediphosphate-glucose, glucose-1-phosphate, adenosine, nicotinamide-adenine-diphosphate, etc.
- derivatives of carbohydrates such as nitrocellulose
- complex polymeric carbohydrates and derivatives such as dextran, glycogen, etc.

Preferred coating materials include cellobiose, pyridoxyl-5-pyrophosphate and citrate.

In a preferred process for coating, the core particles are suspended in a coating solution. The coating solution into which the core particles are suspended contains, for example, from 1 to 30 weight/volume percent of the coating material. The solute is preferably double distilled water (dd$H_2O$). The amount of core particles suspended within the coating solution will vary depending upon the type of particle and its size. Typically, suspensions containing from 0.1 to 10 weight/volume percent are suitable. Suspensions of approximately 1 weight/volume percent of particles are preferred.

The core particles are maintained in dispersion in the coating solution for a sufficient time to provide uniform coating of the particles. Sonication is the preferred method for maintaining the dispersion. Dispersion times ranging from 30 minutes to a few hours at room temperature are usually sufficient to provide a suitable coating to the particles. The thickness of the coating is preferably less than 5 nanometers. Thicknesses of the coating may vary provided that the final core particles include a uniform coating over substantially all of the particle surface.

The particles are separated from the suspension after coating and may be stored for future use or redispersed in a solution containing the DNA or RNA to be attached to the particles. Alternatively, the coated particles may be left in the suspension for further treatment involving attachment of the desired DNA or RNA.

The core particle may be made from a biodegradable ceramic or polymer. The term "biodegradable" as used herein means any core particle which decomposes or otherwise disintegrates after prolonged exposure to a mammalian in vivo environment. To be biodegradable, the core particle should be substantially disintegrated within a few weeks after introduction into the body. Brushite is a preferred biodegradable core particle material.

The DNA or RNA which is applied to the coated particles may be selected from a wide variety of DNA or RNA segments which are used to transfect cells during gene therapy. Antisense fragments may also be used.

Exemplary transfection gene segments include human low density lipid receptor CDNA, human adenosine deaminase CDNA, human dystrophan CDNA, and antisense HIV reversed DNA—all subcloned within appropriate expression vectors. The DNA or RNA transfection segments may be prepared according to known procedures such as the procedure described in Manniatis, T., Fritsch, E. F., and Sambrook, S., *Molecular Cloning*, Cold Spring Laboratory Press, New York., 1.0–19.0 (1989). Gene segments are also available commercially from a number of different suppliers.

The procedure for attaching gene segments or antisense fragments to the coating on the core particles involves suspending the coated core particles in an aqueous solution containing the gene segments. The presence in the solution of materials that may preferentially attach to the particle surface is often not advantageous. For example, the dispersion agents present in the solution may create an undesirable coating on the suspended particles prior to protein attachment. Water miscible solvents such as methanol or ethanol may be used. The aqueous solution of coated microparticles can be agitated sufficiently to provide a uniform suspension of the particles. Typically, the amount of particles in solution will be between about 0.5 mg per milliliter of solution and 5 mg per milliliter of solution. Sonication is a preferred method for providing a uniform suspension of the coated particles in solution.

The suspension of coated particles and gene segments must be within certain parameters for segment attachment and self assembly to occur. The temperature of the particle solution should be between 1° C. to 45° C. The gene segments or antisense fragments may be bound to the coated particles in distilled water. The oxygen tension of the solution is preferably less than 10% in a solution sparged initially by helium and then gassed with helium, nitrogen and carbon dioxide. The pH of the solution is preferably slightly acidic (relative to blood), with a value, preferably, of between 6.8 to 7.2. An exemplary solution for dispersion of the coated microparticles and for DNA attachment is an aqueous solution containing: 0.0360 milligrams $MgSo_4$ per liter, 0.0609 milligrams $MgCl_{2.6}H_2O$, 0.0441 milligram CaCl$_2$.2H$_2$O, 22.823 grams K$_2$HPO$_4$, 13.609 grams KH$_2$PO$_4$, 7.455 grams KCl, and 4.101 gram sodium acetate. The pH of this solution is adjusted to 6.8.

The coated particle cores with the attached gene segment or antisense fragment can be separated from the ionic growth medium and stored for further use. The coated particles may be stored by any of the conventional methods typically used for storing gene segment or antisense fragments. For example, the coated particles may be freeze dried or stored as a suspension in a compatible solution. When used in gene therapy, the particles coated with a targeting layer as described below, are injected or otherwise administered to the individual according to conventional procedures. Any pharmaceutically acceptable carrier solution or other compound may be used in administering the DNA/RNA coated particles to the individual. When used in vitro, the DNA/RNA coated particles are suspended in solution and used in the same manner as other gene therapy compounds. The same is true for use of antisense coated particles. The same protocol and procedures well known for gene therapy to introduce genes into cells both in vivo and in vitro may be used wherein the DNA/RNA/antisenseparticle constructs of the present invention are substituted for other gene therapy compounds.

Targeting of the coated particle and attached gene support or antisense fragment is accomplished by coating the particles with a phospholipid membrane complex which includes ligands that are reactive with receptors on particular cells. Exemplary target ligands include HIV coat proteins (gp160, 41, 120) corona virus coat proteins, EBV coat proteins (gp350). Any membrane bound ligand/receptor may be used. These ligands are attached to the particle complex in the same manner as attachment of the transfection agents discussed above.

The lipids used to coat the biodegradable nanocrystalline particle and bound transfection agent are the same lipids commonly used to form liposomes. Suitable lipids include phospholipids such as phosphatidylcholine, cholesterol and phosphatidylserine. The lipid layer is applied to the nanocrystalline core particle and bound to a biologically active agent in the same manner as the other coatings are applied, i.e. by adsorption onto the surface.

The core particle and bound agent do not need to be totally covered with a lipid layer. Preferably, the amount of lipid used to coat the particle will be sufficient to coat the entire particle. The combined layer of lipid and targeting ligand provide for targeting of the core particle and attached gene segments to the corresponding cell receptor.

The preferred transfection nanoparticles are selfassembling complexes of nanometer sized particles, typically on the order 100 nm, that carry an inner layer of transfecting DNA or RNA and an outer layer of targeting molecules. Functionally, the targeting molecules, usually referred to as ligands, impart tissue specificity in the same way a virus finds its host, i.e., the ligands promote the association of the transfection nanoparticles to a cell surface by binding to cell surface receptor molecules.

Construction of the transfection nanoparticles is a simple process and which occurs spontaneously without apparent covalent modification. In one exemplary synthesis, nanoparticle dispersions of tricalcium phosphate (TCP) are prepared from isochoric opposing streams of 0.750M Calcium Chloride and 0.25M monobasic Sodium Phosphate. The resulting precipitant is sonicated at 175 Watts at room temperature for 30 minutes and washed in volumes of 20 mM pH 6.80 phosphate buffer before being mixed with Cesium Chloride purified transfecting DNA, RNA or antisense. The DNA, RNA or antisense is then left to adsorb to the particulate surfaces at room temperature under mild agitation. After the transfection agent attachment step is completed, membrane specific ligands, typically prepared from the envelopes of retroviruses, are added to the dispersion and allowed to adsorb overnight at 4.0° C. in a stir cell.

The ligand receptor complex can be chosen so as to be unique for the targeted tissue since tissues can be differentiated by their component cells, cell surface receptors, and complementary ligands. Once the interaction takes place, transfection can proceed through a range of cellular uptake mechanisms, resulting in the dissolution of the DNA (RNA/antisense) away from the particle complexes, recombination, and expression in a target cell. Introducing DNA, RNA or antisense by this method allows for the alteration of the phenotype of specific cells in a targeted tissue. It will occur because of the conformational stability of the ligands employed, the integration locus of the transfecting DNA/RNA/antisense, and the expression ability of transfecting DNA (RNA/antisense) in the targeted tissue.

Ligand preparation is as varied as their source. They can be produced by recombinant means or derived from their natural source. Preferably, viral envelope ligands are extracted from viruses, such as Human Immunodeficiency Virus, Epstein-Barr Virus, and murine ecotropic viral strains. In general, the viral envelopes are extracted in accordance with known procedures and then combined with phospholipids in a phosphate buffer. The solution of viral envelopes and phospholipids are then added to the suspension of DNA/RNA coated nanoparticles. The viral envelopes and phospholipids are absorbed onto the nanoparticles to form a targeting membrane.

Typical preparations of transfection nanoparticles yield in the neighborhood of a tenth of a microgram of DNA (and RNA) per microliter of dispersion as gauged by spectrophotometric determinations over time. If higher concentrations are required, the DNA (and RNA) is premixed with the substrate solutions and is allowed to slowly coprecipitate with the core material at a pH of 6.5. The particulate size is controlled by the time wise addition and surface adsorption of membrane ligands, and by the removal of substrate by ultrafiltration dialysis. Independent of the synthetic route chosen, administration of the transfection nanoparticles is accomplished by both enteral and parenteral routes. The doses are the same as those used in gene therapy.

The nanoparticle-DNA/RNA constructs of the present invention may be made without the targeting layer when receptor mediated targeting is not required. For example, the constructs may be prepared without the targeting layer when calcium channel uptake of DNA/RNA or other non-cell receptor uptake is desired. The small size of the constructs allows them to evade the reticular endothelial system, thereby increasing the circulation time and transfection efficiency.

The following non-limiting examples describe certain aspects of the present invention in greater detail.

Example 1

Preparation of nanocrystalline tin oxide microparticles:

1.5 to 2.0 mg of ultrafine (nanocrystalline) metal powder was placed in a 1.7 ml screwcap microcentrifuge with 1.5 mls of double distilled water (ddH$_2$O). The ddH$_2$O was filtered through a rinsed 0.45 micron filter-sterilizing unit or acrodisc (Gelman Scientific). The metal powder was tin oxide with a mean diameter (by photon correlation spectroscopy) of 140 nm. The mixture was vortexed for 30 seconds and placed into a water sonicating bath overnight. The sonication bath temperature was stabilized at 60° C. After a 24-hour sonication, the samples were vortexed once more for 30 seconds with the resulting dispersion clarified by microcentrifugation at approximately 16,000 rpm for 15 seconds. The analysis of particle size was carried out on a Coulter N4MD sub-micron particle analyzer.

The coating was applied to the tin oxide particles by suspending the particles in a stock solution of cellobiose. The cellobiose stock solution was a 292 mM solution made by dissolving 1.000 gram of cellobiose in 9.00 mls of ddH$_2$O. Solution was accomplished at approximately 70° C. in order to promote quick dissolution. The resulting cellobiose solution was filter sterilized through a rinsed 0.45 micron filter with the final volume being adjusted to 10.00 ml.

Sufficient cellobiose stock solution was added to 150 microliters of ultrafine tin oxide dispersion so that the final concentration of the tin oxide was 1.00 percent (w/v) or 29.2 mM. A typical volume for preparation was 2.0 mls which was mixed four or five times by the action of a micropipetor. After mixing, the dispersion was allowed to equilibrate for two hours. Demonstration of successful coating of the particles was provided by measuring the mobility of the particles (coated and uncoated) on a Coulter DELSA 440 doppler energy light scatter analyzer. The coated tin oxide particles exhibited a relatively low mobility compared to the non-coated tin oxide particles. Measurements were also taken at various dilute salt concentrations to ensure that the observations with respect to mobility were not artifactual. The tests demonstrate that the particles were coated with the cellobiose.

The coated particles are then used to attach antigenic proteins, peptides or pharmacological agents to prepare bioreactive particles.

Example 2

Preparation of nanocrystalline ruthenium oxide particles:

The same procedure was carried out in accordance with Example 1, except that ruthenium oxide microparticles were substituted for the tin oxide particles. The ruthenium oxide particles were obtained from Vacuum Metallurgical Company (Japan).

Example 3

Preparation of the nanocrystalline silicon dioxide and tin oxide particles:

Nanocrystalline silicon dioxide was acquired commercially from Advanced Refractory Technologies, Inc. (Buffalo, N.Y.) and tin oxide was acquired commercially from Vacuum Metallurgical Co. (Japan). The tin oxide particles were also prepared by reactive evaporations of tin in an argon-oxygen mixture and collected on cooled substrates. Nanocrystalline tin oxide was also synthesized by D.C. reactive Magnetron sputtering (inverted cathode). A 3" diameter target of high purity tin was sputtered in a high pressure gas mixture of argon and oxygen. The ultrafine particles formed in the gas phase were collected on copper tubes cooled to 77° K. with flowing liquid nitrogen. All materials were characterized by X-ray diffraction crystallography, transmission electron microscopy, photon correlation spectroscopy, and Doppler electrophoretic light scatter analysis. X-ray diffraction samples were prepared by mounting the powder on a glass slide using double-sized Scotch tape. CuK$\alpha$ radiation was used on a Norelco diffractometer. The spectrum obtained was compared with ASTM standard data of tin oxide. (Powder Diffraction File, Card #21-1250. Joint Committee on Power Diffraction Standards, American Society for Testing and Materials, Philadelphia 1976.) The specimens for (TEM) were collected on a standard 3 mm diameter carbon coated copper mesh by dipping into a dispersion of the (UFP's) in 22-propanol. The samples were examined on a JEOL-STEM 100 CX at an acceleration voltage of 60–80 KV.

To create working dispersions of these metal oxides, 1.5 to 3.0 mg of metal oxide powder was added to 1.5 ml double distilled H$_2$O in a dust-free screw top microcentrifuge tube (Sarsted) and vortexed for 30 seconds. The mixture was then sonicated for 16 to 24 hours followed by a second 30 seconds vortex. The submicron fraction was then isolated by pelleting macroparticulates by microcentrifugation 16,000×g for 15 seconds. Approximately 1.3 ml of supernatant was then removed and placed in another dust-free screw top microcentrifuge tube. A sample was prepared for photon correlation spectroscopy (Coulter N4MD) and Doppler electrophoretic light scattering (Coulter delsa 440) analysis by removing 50 to 100 µl of the dispersion and placing it in a polystyrene cuvette and diluting it to a final volume of 1.00 ml with ddH$_2$O. The stability of the dispersion was determined by sequential measurements over a 24-hour period and was found to be stable. The stability of the dispersion with respect to progressive salinity of the solvent (increasing conductivity) was similarly determined. The stability increased with progressive salinity of the solvent.

1.00 ml of the dispersion was combined and stirred with 8.00 ml of ddH$_2$O and 1.00 ml of 29.2 mM cellobiose stock in a 15.0 ml capacity ultrafiltration stir cell (Spectra) which has been fitted with a pre-rinsed 5×10$^5$ molecular weight cutoff type F membrane (Spectra). The sample was then left to stir for 15 minutes. After stirring, the excess cellobiose was removed by flushing through the cell chamber 250 ml of ddH$_2$O by the action of a peristaltic pump at a rate that does not exceed 10.0 ml/min. After washing, the filtrate was concentrated by the means of pressurized N$_2$ gas to approximately 1.0 ml. Character was established by the removal of 500 µl of the treated dispersion by N4MD analysis. The mean dispersion diameter was re-established at this step. The stability of the coated dispersion was determined by sequential measurements over a 24-hour period. The stability of the coated dispersion with respect to progressive salinity of the solvent (increasing conductivity) was similarly determined.

The resulting coated nanocrystalline particles are suitable for attachment of various proteins, peptides and pharmaceutical agents.

Example 4

Preparation of Tricalcium Phosphate (TCP) Nanocrystalline Particles Coated With P5P:

1. Using two 60 cc syringes and a T-Luer lock, inject 50 mls of 0.75 m CaCl$_2$ and 50 mls of 0.25 m Na$_2$HPO$_4$ into a 120 ml pharmaceutical bottle in the cup sonicator. Sonicate for 30 minutes at room temperature to form suspension of TCP particles.

2. Spin the TCP preparation down in the centrifuge using the bucket rotor at 3000 rpm for 15 minutes to remove unreacted components.

3. Resuspend the TCP particles in 50 mls of HPLC grade water and mix well. Spin down at 3000 rpm for 15 minutes. Repeat step 3, three times (3×).

4. Add 1.0 ml of 100 mg/ml pyridoxal-5-phosphate (P5P) and incubate for 30 minutes on a rocker arm at room temperature.
5. Lyophilize overnight.
6. Resuspend the P5P-TCP preparation in 50 mls of 0.1 n sodium hydroxide. Mix well. Spin down at 3000 rpm for 20 minutes. This removes the excess P5P. (This step may not have to be completed with all carbohydrates. Centrifugation and subsequent washing steps may be adequate.)
7. Resuspend in 50 mls of PBS and spin down at 3000 rpm for 15 minutes. Repeat step 8 three times (3×). This removes the sodium hydroxide.
8. Resuspend pellet in 50 mls of HPLC grade water and spin down at 3000 rpm for 15 minutes. Repeat step 9 three times (3×). This removes the PBS.
9. Resuspend the pellet in 4.0 mls of HPLC water and 1.0 ml of 100 mM of sodium citrate to pH 7.2.
10. Sonicate for 15 minutes at room temperature to form suspension of particles which is ready for attachment of biochemically active agent.

Example 5

Preparation of TCP Nanocrystalline Particles Coated with Cellobiose:

The same procedure as described in Example 1 is followed except that cellobiose is substituted for P5P. The cellobiose coating is applied to the particles by suspending the particles in a stock solution of cellobiose. The cellobiose stock solution is a 292 mM solution made by dissolving 1.000 gram of cellobiose in 9.00 mls of $ddH_2O$. Solution is accomplished at approximately 70° C. in order to promote quick dissolution. The resulting cellobiose solution is filter sterilized through a rinsed 0.45 micron filter with the final volume being adjusted to 10.00 ml.

Sufficient cellobiose stock solution is added to 150 microliters of the ultrafine biodegradable particle dispersion so that the final concentration of the particle is 1.00 percent (w/v) or 29.2 mM. A typical volume for preparation is 2.0 mls which is mixed four or five times by the action of a micro-pipetor. After mixing, the dispersion is allowed to equilibrate for two hours. Demonstration of successful coating of the particles is provided by measuring the mobility of the particles (coated and uncoated) on a Coulter DELSA 440 doppler energy light scatter analyzer. The coated particles exhibit a relatively low mobility compared to the non-coated particles. Measurements are also taken at various dilute salt concentrations to ensure that the observations with respect to mobility are not artifactual.

The coated particles are then used to attach antigenic proteins, peptides or pharmacological agents to prepare bioreactive particles.

Example 6

Preparation of Nanoparticles with Cellobiose or P5P Coatings:

The tin oxide, ruthenium oxide and silicon dioxide nanoparticles prepared in Example 1–3 are coated with cellobiose or P5P in the same manner as TCP.

Example 7

Preparing Meticulously Clean Biodegradable Nanoparticles:
1. Prepare 6 clean sonication tubes with 500 mg of biodegradable particles per tube.
2. In fume hood, fill tubes with HCl (10N) approx. 8 ml/tube.
3. Sonicate for 30 min. (full power [175 watts]/25° C.); three tubes per sonication treatment.
3. Centrifuge 30 min. at 2000 rpm.
5. Decant the acidic supernatant (in the fume hood), fill the tubes with HPLC grade water and then vortex.
6. Sonicate for 30 min [above conditions] and centrifuge for 30 [centrifuging is complete if the supernatant is clear].
7. Decant the supernatant, and fill the tubes with HPLC grade water and vortex.
8. Repeat steps 7 and 8 two more times.
9. Decant the preparation into a clean glass [pyrex] baking dish.
10. Anneal at 210° C. overnight.
11. Remove the dried biodegradable crystals by gentle scraping with a clean unpainted spatula and transfer into 6 clean glass sonicating tubes.
12. Repeat steps 3 through 8.
13. Prepare a 10 kD (NMWL) 150 ml ultrafiltration cell, empty the contents only one[no more than 500 mg per filtration run] of the tubes into the cell, and wash 500 ml of HPLC grade water through the cell under a $N_2$ pressure head of 20 psi (regulator pressure gauge reading).
14. After washing, adjust the preparation volume to 100.0 ml by using the appropriate volume markings on the side of the cell.
15. Take a concentration measurement by removing 1.0 ml of the preparation from the cell and lyophilizing it down in a pre-weighed 1.7 ml Eppendorf tube. After lyophilization, take a mass measurement of the tube with its contents and subtract it away from the mass of the empty tube. This provides the initial density of the preparation. Preferably, the concentration or density of the particles in the solution is about 10 mg/ml. If the initial density is lower than 10 mg/ml, then the solution should be further concentrated in the ultrafiltration cell.

Example 8

Coating Meticulously Clean Biodegradable Nanoparticles with a Molecular Stabilizing Film (Cellobiose): Incubation/Lyophilization.
1. Sonicate the meticulously clean biodegradable particles (aqueous dispersion) prepared in Example 7 for 30 minutes at 25° C. at full power [175 Watts].
2. Then as quickly as possible, exchange suspending medium from water (stock) to a solution of 500 mM cellobiose using either a bench top microcentrifuge (30 seconds, full speed of 14,000 RPM) for small volumes or for larger volumes a floor models centrifuge (model 21K, in 50 ml centrifuge tubes, 8,000 RPM for a maximum of 2 minutes) Suspend the pelleted particles with 500 mM cellobiose, sonicate to aid dispersion (approximately 5 minutes at 25° C. at full power [175 Watts]) and finally set the mixture on a rocking plate overnight in a cold room [4° C.]
3. The next day portion out the mixture into appropriately sized vessels for overnight lyophilization.
4. Leave the tubes capped with a layer of parafilm around the cap and place them in a freezer until the washing step.

5. Reconstitute the particle/cellobiose in a suitable buffer depending on the application. Suitable buffers are low ionic strength buffered phosphate (PRB), water, or bicarbonate. Reconstitution in the buffer is accomplished by vortexing and a 5 minute sonication [175 Watts/25° C.].
6. Wash by repeated centrifugation (using either a bench top microcentrifuge [30 seconds, full speed of 14,000 RPM] for small volumes or for large volumes a floor model centrifuge [model 21K, in 50 ml centrifuge tubes, 8,000 RPM for a maximum of 2 minutes]) and resuspension into the buffer.
7. Take a concentration measurement by removing 1 ml of the suspension dehydrating it in a lyophilizer in a pre-weighed 1.7 ml Eppendorf tube, and massing.
8. Calculate the final volume necessary to bring the concentration to 1 mg/ml. Add enough buffer to bring the concentration of the particle/cellobiose preparation to 1 mg/ml.

Example 9

Preparing Meticulously Clean Particles of Brushite:
Reagents.
0.75M $CaCl_2$: 55.13 g $CaCl_2.2H_2O$ is dissolved with HPLC grade water to 0.500 L in a volumetric flask. Filter sterilize with 0.2 um sterile filtration unit and place in a sterile 500 ml culture medium flask. Store at room temperature.
0.25M $Na_2HPO_4$: 17.75 g of anhydrous $Na_2HPO_4$ is dissolved with HPLC grade water to 0.500 L in a volumetric flask. Filter sterilize with 0.2 um sterile filtration unit and place in a sterile 500 ml culture medium flask. Also store at room temperature.
Brushite synthesis.
About a half hour before synthesis, prepare the sonicator by cooling down the cup horn. This is accomplished by adjusting the low temperature thermostat on the water condenser to 4° C. and dialing a setting of "4" on the peristatic circulator. Once the 4° C. mark is reached, prepare 50.0 ml of 0.75M $CaCl_2$ and 50.0 ml of 0.25M $Na_2H_2PO_4$ and load into 50 ml syringes. The syringes are then to be connected to a 3-way luer lock connector so that they are set in diametric opposition—allowing the remaining luer port to be free to dispel product. Once the mixing apparatus is set up, place a sterile 120 ml sonicating flask in the cup horn and slowly power up the sonicator to 100% power. Position the mixing apparatus so that the free luer port is over the sonicating flask. Expel syringe contents into the flask as rapidly and evenly as possible so as to empty each syringe roughly at the same time. Then quickly secure a polypropylene liner over the sonicating flask and let sonicate for an additional 15 minutes.
Brushite washing.
Roughly divide the preparation into two 50 ml blue top polypropylene tubes and pellet at 2000 rpm for 10 minutes (room temperature). Reconstitute by vortexing each pellet with sterile HPLC grade water to 50 ml (or tube capacity) and pellet at 2000 rpm for 10 minutes. Repeat this wash 3 more times and reconstitute the last pellets to 50.0 ml. Transfer the dispersion to a sterile 120 ml sonicating flask with polypropylene liner. Place the flask in a previously cooled sonicator cup horn at 1° C. Sonicate at 100% power for 60 minutes.

Example 10

Coating Meticulously Clean Particles of Brushite with a Molecular Stabilizing Film of Pyridoxyl-5-Pyrophosphate:
Brushite/Pyroxidal 5 phosphate (vitamine B6).

Pellet 100 ml of the dispersion prepared in Example 10 so that the entire contents can be transferred to a 50 ml conical tube. Adjust the tube volume to 40.0 ml. Then transfer the contents in 10 ml aliquots to four 15 ml conical tubes. Dissolve 1000 mg of Pyroxidal-5-phosphate with 800 μl of 10N NaOH and adjust with water to 10 mls. Filter sterilize this clear yellow solution with a 0.2 μm acrodisc and add 2.5 ml aliquots to each of the previously prepared 4 brushite tubes. Vortex each tube a few seconds to make certain that the contents are well dispersed. Lyophilize overnight [approx. 16 hrs] at the low drying rate setting. The next morning resuspend in 50 ml aliquots of sterile HPLC grade water five more times. Pellet once more and transfer the pellets to four 15 ml conical tubes and adjust the final preparation volume with water to 40.0 ml.

Example 11

Coating Meticulously Clean Particles of Brushite With a Molecular Stabilizing Film of Citrate:
Brushite/citrate.
Pellet the 100 ml of the dispersion prepared in Example 13 so that entire contents can be transferred to a 50 ml conical tube. Adjust the tube volume to 40.0 ml. Then transfer the contents in 10 ml aliquots to four 15 ml conical tubes. Add 10 ml of 100 mM citrate to each of the 15 ml conicals and nutate for 30 minutes at room temperature. Lyophilize overnight [approx. 16 hrs] at the low drying rate setting. The next morning resuspend in 50 ml aliquots of sterile HPLC grade water five more times. Pellet once more and transfer the pellets to four 15 ml conical tubes and adjust the final preparation volume with water to 40.0 ml.

Example 12

Attachment of Transfection Agents:
The following procedure is used to attach DNA or RNA segments to any of the coated particles described in the preceding Examples:
A dispersion of 40 mg/ml of coated nanoparticles in 20 mM pH 6.80 phosphate buffer is prepared. To this dispersion, 1.00 ug of cesium chloride purified DNA or RNA fragments are added and left to absorb at room temperature under mild agitation for approximately 16 hours. Specific DNA fragment used in this example is the human deaminase gene.

Example 13

Attachment of Targeting Ligands and Phospholip Membrane:
The procedure described in the example for isolating and attaching the targeting ligands and phospholip membrane may be used for all of the particle/coating/DNA or RNA combinations set forth in the preceding examples.
$10^6$ transforming units of virus is incubated with Triton extraction buffer (1.0% of Triton×100/0.25 mM DTT\10 mM Tris pH 7.4\1.0 mM MgCl). Extract is then ultracentrifuged at 100K*g for 2.0 hrs (35 rpm SW50.1 Beckman rotor) at 4.0° C. to remove nucleocapsid. Removal of triton and envelope protein enrichment is accomplished by incubation with a 300 ul slurry of polystyrene micro beads (Spectra Gel D2) and subsequent 100 kD ultrafiltration into phosphate buffer 5 mg/ml of phosphotidyl choline and 5 mg/ml phosphotidyl serine. An alternative method of viral extraction is as follows. A mixture of phosphotidyl choline (5 mg/ml) and phosphotidyl serine (5 mg/ml) in 20 mM pH 7.4 phosphate buffer is sonicated for 30 minutes at 4.0° C.

$10^6$ units per ml of virus is then added to 1.0 ml of the phospholipid mixture and left to sonicate at 5 sec cycles per minute for 30 minutes at 4.0° C. Nucleocapsid is removed by ultracentrifugation at 35 krpm at 4.0° C. Intervening layers of carbohydrate may be first adsorbed to the TCP-DNA/RNA complex prior to the addition of the ligand/membrane components.

Example 14

A construct is composed of a brushite core with an adsorbed first layer consisting of human deaminase gene in an expression cassette with a albumin enhancer and limited terminal repeats for genomic integration. The construct includes an adsorbed second layer of cellobiose and an adsorbed third layer of membrane proteins from human low density lipids (LDL receptor ligands).

The entire contents of all references cited hereinabove are hereby incorporated by reference.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A composition of matter comprising:

a biodegradable core particle having a diameter of less than about 1000 nanometers wherein said core particle comprises a biodegradable ceramic or polymer;

a coating comprising a substance that provides a threshold surface energy to said core particle which is sufficient to bind transfection agents without denaturing said agents, said substance covering at least a part of the surface of said core particle and wherein said substance is selected from the group consisting of carbohydrates, citrate, fumarate, succinate, isocitrate, oxalacetate, realate, pyridoxyl-5-pyrophosphate, thiamine pyrophosphate, uridine-diphosphate-glucose, glucose-1-phosphate, adenosine and nicotinamide-adenine-diphosphate;

at least one transfection active agent bound to said coated core particle wherein said transfection agent bound to said coated core particle is not denatured.

2. A composition of matter according to claim 1 wherein said core particle comprises brushite.

3. A composition of matter according to claim 1 which further includes a target coating covering at least a portion of the surface of said core particle.

4. A composition of matter according to claim 3 wherein said outer target coating comprises a phospholipid and targeting ligand.

5. A composition of matter according to claim 1 wherein said coating comprises a carbohydrate.

6. A composition of matter according to claim 1 wherein said coating comprise cellobiose, pyridoxal-5-phosphate or citrate.

7. A composition of matter according to claim 1 wherein said transfection agent is a DNA or RNA segment.

8. A composition of matter according to claim 1 wherein said transfection agent is an antisense fragment.

9. A composition of matter according to claim 4 wherein said targeting ligand is a viral envelope.

10. A composition of matter according to claim 3 wherein said core particle is brushite.

11. A composition of matter according to claim 3 wherein said coating comprises a carbohydrate.

12. A composition of matter according to claim 3 wherein said coating comprises cellobiose, pyridoxal-5-phosphate or citrate.

13. A composition of matter according to claim 3 wherein said transfection agent is a DNA or RNA segment.

14. A composition of matter according to claim 3 wherein said transfection agent is an antisense fragment.

15. A composition of matter according to claim 1 wherein said carbohydrate is selected from the group consisting of sucrose, cellobiose, nystose, triose, dextrose, trehalose, glucose, lactose, maltose, dextran, nitrocellulose and glycogen.

16. A composition of matter according to claim 3 wherein said carbohydrate is selected from the group consisting of glucose, sucrose, cellobiose, nystose, triose, dextrose, trehalose, lactose, maltose, dextran, nitrocellulose and glycogen.

* * * * *

UNITED STATES PATENT AND TRADEMARK OFFICE
CERTIFICATE OF CORRECTION

PATENT NO. : 5,460,831
DATED : October 24, 1995
INVENTOR(S) : Kossovsky et al.

It is certified that error appears in the above-indentified patent and that said Letters Patent is hereby corrected as shown below:

Column 15, line 41, "realate" should be "malate"

Signed and Sealed this

Twentieth Day of February, 1996

Attest:

BRUCE LEHMAN

*Attesting Officer*     *Commissioner of Patents and Trademarks*